United States Patent [19]

Kalopissis et al.

[11] 4,101,576

[45] Jul. 18, 1978

[54] 2-CARBAMYLMETHYL-OR (DIETHYLCARBAMYL)METHYL-AMINO-4-HYDROXY TOLUENE AND PROCESS FOR PREPARING THE SAME

[75] Inventors: Gregoire Kalopissis, Neuilly-sur-Seine; Andreé Bugaut, Boulogne-sur-Seine, both of France

[73] Assignee: L'Oreal, Paris, France

[21] Appl. No.: 762,329

[22] Filed: Jan. 25, 1977

Related U.S. Application Data

[60] Continuation of Ser. No. 619,478, Oct. 3, 1975, abandoned, which is a continuation-in-part of Ser. No. 263,625, Jun. 16, 1972, abandoned, which is a continuation of Ser. No. 848,342, Aug. 7, 1969, abandoned, which is a division of Ser. No. 525,291, Feb. 7, 1966, Pat. No. 3,591,323.

[30] Foreign Application Priority Data

May 6, 1965 [FR] France .................. 65.16140

[51] Int. Cl.² ............... C07C 103/29; C07C 103/76

[52] U.S. Cl. .................. 260/559 A; 260/575; 8/10; 8/10.1

[58] Field of Search .................... 260/559 A, 575

[56] References Cited

U.S. PATENT DOCUMENTS 3,563,684   2/1971   Charle et al. ................. 8/11

FOREIGN PATENT DOCUMENTS 82,233   8/1905   Fed. Rep. of Germany.

OTHER PUBLICATIONS

Beilstein's Handbuch der Chemie, vol. XIII, pp. 598–599 (1930).
Corbett, Venkataramann's Chemistry of Synthetic Dyes, vol. V, pp. 478–493 (1971).

*Primary Examiner*—Daniel E. Wyman
*Assistant Examiner*—Thomas A. Waltz
*Attorney, Agent, or Firm*—Cushman, Darby & Cushman

[57] ABSTRACT

The dye coupling compounds 2-carbamylmethylamino-4-hydroxy toluene and 2-diethylcarbamylmethylamino-4-hydroxy toluene.

5 Claims, No Drawings

2-CARBAMYLMETHYL-OR (DIETHYLCARBAMYL)METHYL-AMINO-4-HYDROXY TOLUENE AND PROCESS FOR PREPARING THE SAME

This application is a continuation of application Ser. No. 619,478, filed Oct. 3, 1975 now abandoned which in turn is a continuation-in-part of our application Ser. No. 263,625 filed June 16, 1972, now abandoned, which is a continuation of application Ser. No. 848,342, filed Aug. 7, 1969, now abandoned, which is a division of Ser. No. 525,291 filed Feb. 7, 1966, now U.S. Pat. No. 3,591,323.

Hair dyes having a substituted or unsubstituted aromatic diamine base have been used for a long time. The substitutions are on the aromatic ring or the nitrogen atoms of the amino groups. Coupling substances are added to these diamine bases to vary the color obtained.

It is known that the addition of certain coupling substances to such aromatic paradiamines makes it possible to obtain particularly stable and long-lasting colorations, while the shades obtained with the bases alone change rapidly. Moreover, certain of these bases are not dyes in themselves, but are effective only when suitably coupled.

Among the known substances conventionally coupled with aromatic paradiamines is meta-amino-phenol, which unfortunately frequently produces hair dyes which do not last very long. The present invention proposes a new class of meta-amino-phenols for use as coupling substances, which make it possible to obtain especially stable long-lasting colorations, which resist exposure to the light and to outside agents, and enlarge the range of shades in the blue section of the spectrum which may be obtained by associating an aromatic paradiamine and a meta-amino-phenol.

The object of the present invention is to provide coupling compounds which form new dyes for keratinic fibers, and particularly for hair, said new dyes are essentially characterized by the fact that they are the reaction product of at least one aromatic paradiamine having the formula:

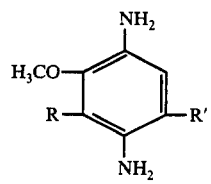

(I)

in which R and R' are hydrogen or methyl but R' cannot be hydrogen when R is methyl, and at least one meta-amino-phenol coupling substance having the following formula:

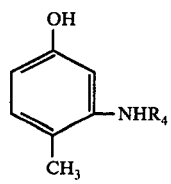

(II)

in which $R_4$ is selected from the group consisting of carbamylmethyl and diethyl-carbamylmethyl.

This invention is directed to the new coupling compounds of formula II set forth above.

A characteristic feature of the invention resides in the fact that in the dyeing solution the ratio between the molecular concentration of the bases used and that of the coupling substances used is generally close to, but preferably less than 1.

If the coupling compound of formula II is not present in a molar excess with relation to the base compound of formula I the hair dye compositions tend to cause toxic or allergy reactions when they contact the skin. When these compositions contain a molar excess of the coupling compound the dye compositions do not cause toxic or allergy reactions.

The said dyeing solution is utilized in a conventional manner, by bringing it to an alkaline pH, with ammonia, for example, and applying it to the hair in the presence of an oxidizing solution which preferably is a hydrogen peroxide solution.

The dyeing solution may also contain other dyes which may be used under the same conditions as direct dyes for keratinic fibers, for example azo or anthraquinone dyes, or dyes obtained by associating bases and coupling substances other than those with which the present invention is concerned.

The dyeing solutions may also contain wetting, dispersing or penetrating agents, and other ingredients commonly included in hair dyes. The product may take the form of an aqueous solution, a cream or a gel.

A very broad range of colors within the blue portion of the spectrum may be obtained by associating a coupling substance of this invention with an aromatic paradiamine, and when an aromatic paradiamine is used with a combination of two coupling substances according to the invention, all the shades between those which can be obtained by associating any of the single coupling substances with the base may be secured by varying the proportion between the two coupling substances.

Another object of the invention is the new method of dyeing the hair with these new dye compositions which comprises the steps of adding hydrogen peroxide, applying a dye of the above-defined type, and then rinsing, shampooing, washing and drying the hair.

A still further object of the invention is to provide new methods of preparing the meta-amino-phenols responding to formula II.

The process of preparing 2-amino-4-hydroxy-toluene is essentially characterized by the fact that paracresol is reacted with an agent capable of protecting the phenol function, preferably with methane sulfochloride. The benzene ring is nitrated in the meta position with respect to the phenol function, for example, with a sulfanitric mixture. The nitro radical is reduced so as to transform it into an amino radical and the phenol function is then liberated, with, for example, a sodium hydroxide solution.

The process of preparing 2-carbamylmethylamino-4-hydroxy toluene and 2-(diethylcarbamoyl) methylamino-4-hydroxy toluene is essentially characterized by the fact that in the first case chloracetamide and in the second case N,N-diethylchloroacetamide is reacted with the previously obtained 2-amino-4-hydroxy toluene.

The new compounds of formula II exhibit a significantly improved stability in an ammoniacal and oxidizing solution over structurally similar prior art compounds.

In order that the invention may be clearly understood, several illustrative methods of carrying it out will now be described.

EXAMPLE 1

Preparation of 2-amino-4-hydroxy toluene

This process embodies the reaction shown in the following diagram:

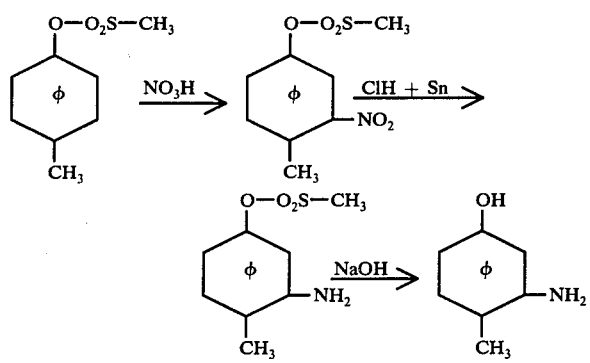

In a first step 4-hydroxy toluene is mesylated by dissolving 2 moles (216 g) of paracresol in 1200 cc of cold pyridine then cool 182 cc (2.4 moles) of methane sulfochloride at a temperature comprised between $-2°$ and $+5°$. Leaving the mixture 2 hours at 5° and 2 hours at ambient temperature, then cooling it in a mixture of ice and chlorohydric acid (4120 g of ice and 1208 cc or 14.2 moles of chlorohydric acid of 1.19 density. The product obtained is dried and embedded in ice (340 g) MP = 41.5° C.

In a second step 2-nitro-4-mesyloxy toluene is prepared by dissolving 0.1 mol (18.6 g) of mesylated 4-hydroxy toluene at a low temperature (0° to 5° C) in 80 cm³ of concentrated sulfuric acid. A sulfo-nitric mixture having the following composition is added at the same temperature:

Nitric acid (density 1.49): 4.7 cm³
Sulfuric acid (density 1.83): 3.8 cm³

The reaction mixture is then poured over ice and the crude product of the reaction dried. After recrystallization in ethanol, the product melts at 105°–106° C. The yield of the reaction is about 89%. Analysis shows the following results:

| Analysis | Calculated for $C_8H_9O_5NS$ | Found |
|---|---|---|
| C% | 41.6 | 41.40 – 41.57 |
| H% | 3.90 | 3.90 – 4.06 |
| N% | 6.06 | 6.13 – 6.10 |

In a third step, the 2-amino-4-mesyloxy toluene is prepared by reducing 0.86 mol (198 g) of 2-nitro-4-mesyloxy toluene by adding a mixture of tin and hydrochloric acid. The reaction mixture is cooled and the desired product is precipitated as a chlorostannate, which is the dried and dissolved in water. The product is then subjected to a current of hydrogen sulfide and the tin sulfide formed is eliminated by filtration. The filtrate is vacuum concentrated and the end product is precipitated by cooling, and dried, giving a yield of about 85% of the hydrochloride of 2-amino, 4-mesyloxy toluene.

In a fourth step, the chemical composition which can serve as a coupling substance is prepared, i.e. 2-amino-4-hydroxy toluene. 0.05 mols (12 g) of 2-amino, 4-mesyloxy toluene hydrochloride is treated with 125 cm³ of sodium hydroxide at double normal strength, under reflux for 2 hours in a nitrogen atmosphere. After cooling, the solution is neutralized with hydrochloric acid and the 2-amino-4-hydroxy toluene is dried. The yield of the reaction is about 80%. The product, after recrystallization in ethyl acetate, melts at 159° C.

EXAMPLE 2

Preparation of 2-carbamylmethylamino-4-hydroxy toluene

This process embodies the reaction shown in the following diagram:

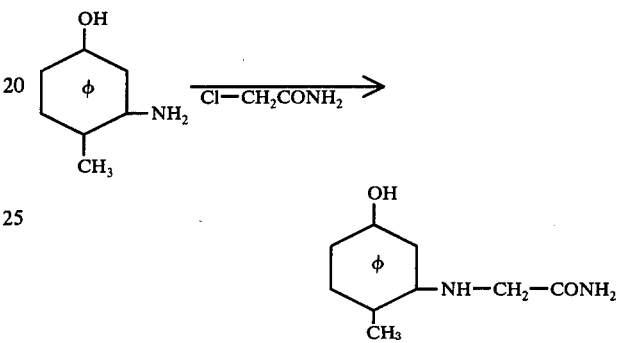

0.405 mol (50 g) of 2-amino-4-hydroxy toluene is dissolved under reflux in 330 cm³ of a hydro-alcoholic solution containing 50% alcohol. 21 g of calcium carbonate is added, plus, little by little, while agitating the mixture under reflux a solution of 0.42 mol of chloracetamide in 345 cm³ of water. Reflux is continued for an hour, and the solution is filtered while boiling to eliminate the mineral salts. The alcohol is eliminated under vacuum. The filtrate is cooled and dried, yielding 68 g of 2-carbamylmethyl-amino-4-hydroxy toluene while, after recrystallization in methylisobutyl-ketone melts at 184° C.

| Analysis | Calculated for $C_9H_{12}O_2N_2$ | Found |
|---|---|---|
| C% | 60.00 | 60.16 – 60.22 |
| H% | 6.66 | 6.76 – 6.67 |
| N% | 15.55 | 15.60 – 15.55 |

EXAMPLE 3

Preparation of 2-(diethylcarbamyl) methyl amino-4-hydroxy toluene

This process embodies the reaction shown in the following diagram:

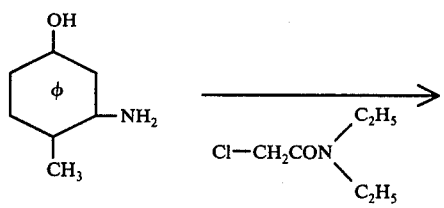

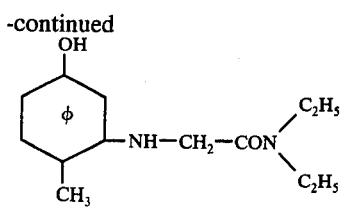

0.05 mol (6.1 g) of 2-amino-4-hydroxy toluene is dissolved under reflux in 40 cm³ of a hydro-alcoholic solution containing 50% alcohol. 2.6 g of calcium carbonate, plus, little by little, while agitating the mixture and under reflux, a solution of 0.051 mol (7.7 g) of N,N,-diethylchloroacetamide in 50 cm³ of water. Reflux is continued for an hour and the solution filtered while boiling to eliminate the mineral salts. The filtrate is then cooled and dried, yielding 8.6 g of 2-(diethylcarbamyl) methyl amino-4-hydroxy toluene, which, after recrystallization in a hydro alcoholic solution containing 50% alcohol melts at 115° C.

| Analysis | Calculated for $C_{13}H_{20}O_2N_2$ | Found |
|---|---|---|
| C% | 66.10 | 66.22 – 66.37 |
| H% | 8.47 | 8.40 – 8.47 |
| N% | 11.86 | 11.70 – 11.79 |

EXAMPLE 4

The following solution is prepared:

| | |
|---|---|
| 1-hydroxy-4-methyl-5-carbamylmethylamino benzene | 0.36 g |
| 2,5-diamino-4-methyl-1-methoxy benzene dihydrochloride | 0.39 g |
| Ammonium lauryl sulfate (having 20% fatty alcohol) | 10.00 g |
| Ammonia at 20% concentration in water | 7 cm³ |
| Water, q.s.p. | 100 g |

This solution is mixed with an equal weight of a 6% by weight hydrogen peroxide solution and applied to white hair. After 20 minutes the hair is shampooed, rinsed, and dried. An intense, slightly violet, blue results.

EXAMPLE 5

The following solution is prepared:

| | |
|---|---|
| 2-amino-4-hydroxy toluene | 1.2 g |
| Paradiaminoanisol sulfate | 1.4 g |
| Ammonia at 20% concentration in water | 10 cm³ |
| Alcohol at 95° | 10 cm³ |
| Water, q.s.p. | 100 cm³ |

This solution is mixed with an equal volume of a 6% by weight hydrogen peroxide solution, and applied to 100% white hair. After 20 minutes the hair is shampooed, rinsed and dried. A strong marine blue shade, which is stable when exposed to the light results.

EXAMPLE 6

The following solution is prepared:

| | |
|---|---|
| 2-carbamylmethylamino-4-hydroxy toluene | 1.8 g |
| 2,5-diamino-4-methyl anisol dihydrochloride | 2.2 g |
| Ammonia at 20% concentration in water | 10 cm³ |
| Alcohol at 95° | 10 cm³ |
| Water, q.s.p. | 100 cm³ |

This solution is mixed with an equal volume of a 6% hydrogen peroxide solution. The mixture is applied to 50% white hair. After 20 minutes the hair is shampooed, rinsed and dried. A deep blue-black shade is obtained, which is stable when exposed to the light.

EXAMPLE 7

The following solution is prepared:

| | |
|---|---|
| 3,6-diamino-2,4-dimethyl anisol dihydrochloride | 16.6 g |
| 2-amino-4-hydroxy toluene | 12.3 g |
| 1-amino-2-nitro-4-N-methylamino benzene | 1.5 g |
| Ammonium lauryl sulfate | 200 g |
| Carboxymethylcellulose | 20 g |
| Disodium salt of ethylene diamino tetra-acetic acid (Trilon B) | 3 g |
| Sodium bisulfite | 4 g |
| Ammonia at 20% | 100 cm³ |
| Water, q.s.p. | 1000 g |

This solution is mixed with an equal volume of hydrogen peroxide and applied to 90% white hair. After waiting 30 minutes, the hair is rinsed, shampooed and dried. A deep violet shade, which is stable when exposed to the light results.

EXAMPLE 8

The following solution is prepared:

| | |
|---|---|
| 3,6-diamino-2,4-dimethyl anisol dihydrochloride | 16.6 g |
| 2-amino-4-hydroxy toluene | 12.3 g |
| Ammonium lauryl sulfate at 20% concentration in water | 200 g |
| Carboxymethylcellulose | 20 g |
| Ethylene diamino tetra-acetic acid | 3 g |
| Sodium bisulfite | 4 g |
| Ammonia at 20% concentration in water | 100 cm³ |
| Water, q.s.p. | 1000 g |

The solution is a thick liquid. It is mixed with an equal volume of a 6% hydrogen peroxide solution and applied to 90% white hair. After 30 minutes, the hair is shampooed, rinsed and dried. The result is a periwinkle violet color, which is stable when exposed to the light.

EXAMPLE 9

The following solution is prepared:

| | |
|---|---|
| Paradiamino anisol sulfate | 13.8 g |
| 2-carbamylmethylamino-4-hydroxy toluene | 18 g |
| 1-amino-2-nitro-4-aminoethyl benzene sulfate | 2 g |
| Ammonium lauryl sulfate at 20% concentration in water | 200 g |
| Carboxymethylcellulose | 10 g |
| Disodium salt of ethylene diamino tetra-acetic acid (Trilon B) | 3 g |
| Sodium bisulfite | 4 g |
| Ammonia at 20% concentration in water | 100 cm³ |
| Water, q.s.p. | 1000 g |

This solution is mixed with an equal volume of a 6% hydrogen peroxide solution and applied to 90% white hair. After waiting 30 minutes the hair is shampooed, rinsed and dried. The result is a mahogany violine shade which is stable when exposed to the light.

EXAMPLE 10

The following solution is prepared:

| | |
|---|---|
| Paradiamino anisol sulfate | 13.8 g |
| 2-diethylcarbamyl-methyl amino-4-hydroxy toluene | 18 g |
| 1-amino-2-nitro-4-amino-ethylamino benzene sulfate | 2 g |
| Ammonium lauryl sulfate at 20% concentration in water | 200 g |
| Carboxymethyl cellulose | 10 g |
| Disodium salt of ethylene diamino tetra-acetic acid (Trilon B) | 3 g |
| Sodium bisulfite | 4 g |
| Ammonia at 20% concentration in water | 100 cm³ |
| Water, q.s.p. | 1000 g |

This solution is mixed with an equal volume of a 6% hydrogen peroxide solution and applied to 90% white hair. The result is a blue-black shade, which is stable when exposed to the light.

What is claimed is:
1. A process for preparing 2-amino-4-hydroxy toluene comprising:
   (1) reacting paracresol in the presence of pyridine with methane sulfochloride at a temperature of about −2° to 5° C to produce a compound having the formula

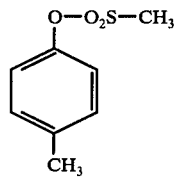

the molar ratio of said cresol to said sulfochloride being 2.0:2.4;
   (2) cooling the compound from step (1) in the presence of a mixture of sufficient ice and chlorohydric acid present in a molar ratio of 14.2 moles per 2 moles of cresol;
   (3) recovering the product of step (2) from the reaction mass and dissolving said separated product at a temperature of 0° − 5° C in concentrated sulfuric acid;
   (4) nitrating the dissolved product of step (3) with a nitrating agent comprising a mixture of nitric acid and sulfuric acid in a ratio of 4.7 cm³:3.8 cm³, respectively, at a temperature of 0° − 5° C to produce a product having the formula

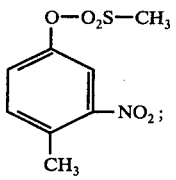

(5) pouring the reaction mixture from step (4) over ice to recover the nitrated product of step (4);
   (6) reducing the —NO₂ substituent on the nitrated product recovered from step (5) to —NH₂ with a reducing agent comprising a mixture of tin and hydrochloric acid;
   (7) cooling the reaction mixture from step (6) thereby precipitating 2-amino-4-mesyloxy toluene as the chlorostannate thereof;
   (8) drying the precipitate from step (7) and dissolving said dried precipitate in water;
   (9) subjecting the dissolved precipitate from step (8) to a current of hydrogen sulfide whereby tin sulfide is formed and thereafter removed by filtration;
   (10) vacuum concentrating the filtrate from step (9) and cooling said concentrated filtrate thereby precipitating the hydrochloride of 2-amino-4-mesyloxy toluene;
   (11) reacting the hydrochloride of 2-amino-4-mesyloxy toluene from step (10) in an inert nitrogen atmosphere with NaOH in amounts of 125 cc per 0.5 mole of said hydrochloride of 2-amino-4-mesyloxy toluene under reflux for about 2 hours; and
   (12) cooling the reaction mixture from step (11) and neutralizing the same with HCl thereby producing 2-amino-4-hydroxy toluene.

2. The process of claim 1 which also includes dissolving the 2-amino-4-hydroxy toluene resulting from step (12) under reflux in a 50% aqueous alcoholic solution in amounts of 0.405 mole of said 2-amino-4-hydroxy toluene per 330 cm³ of said aqueous alcoholic solution, adding calcium carbonate to the resulting solution in amounts of 21 g of said calcium carbonate per 0.405 mole of said 2-amino 4-hydroxy toluene, and while agitating the resulting mixture adding thereto an aqueous solution of chloroacetamide in amounts of 0.42 mole of chloroacetamide in 345 cm³ of water per 0.405 mole of said 2-amino-4-hydroxy toluene, continuing, reflux of the resulting reaction mixture for an hour, filtering said reaction mixture while boiling, cooling and drying the resulting filtrate thereby yielding 2-carbamylmethylamino-4-hydroxy toluene having the formula

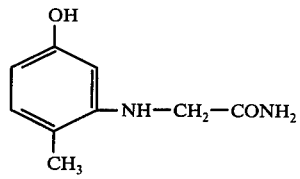

3. The process of claim 1 which also includes dissolving the 2-amino-4-hydroxy toluene resulting from step (12) under reflux in a 50% aqueous alcoholic solution in amounts of 0.05 mole of said 2-amino-4-hydroxy toluene per 40 cm³ of said aqueous alcoholic solution, adding calcium carbonate to the resulting solution in amounts of 2.6 g of said calcium carbonate per 0.05 mole of said 2-amino-4-hydroxy toluene, and while agitating the resulting mixture adding thereto an aqueous solution of N,N-diethylchloracetamide in amounts of 0.051 mole of N,N-diethylchloracetamide in 50 cm³ of water per 0.05 mole of said 2-amino-4-hydroxy toluene, continuing reflux of the resulting reaction mixture for an hour, filtering said reaction mixture while boiling, cooling and drying the resulting filtrate thereby yielding 2-(diethylcarbamyl) methylamino-4-hydroxy toluene having the formula

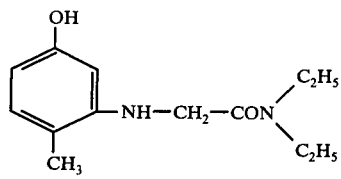

4. 2-carbamylmethylamino-4-hydroxy toluene.
5. 2-(diethylcarbamyl) methylamino-4-hydroxy toluene.

* * * * *